United States Patent [19]

Atwal et al.

[11] Patent Number: 5,011,837
[45] Date of Patent: Apr. 30, 1991

[54] ARYL CYANOGUANIDINES: POTASSIUM CHANNEL ACTIVATORS AND METHOD OF MAKING SAME

[75] Inventors: Karnail Atwal; John R. McCullough, both of Newtown, Pa.; Gary J. Grover, Stockton, N.J.

[73] Assignee: E. R. Squibb & Sons, Inc., Princeton, N.J.

[21] Appl. No.: 349,021

[22] Filed: May 8, 1989

Related U.S. Application Data

[63] Continuation-in-part of Ser. No. 230,209, Aug. 9, 1988, abandoned.

[51] Int. Cl.$^5$ ............... C07D 295/12; C07C 255/00; C07C 239/00
[52] U.S. Cl. ............... 514/227.8; 514/235.8; 514/255; 514/315; 514/307; 514/609; 544/59; 544/106; 544/388; 546/153; 546/189; 558/419; 564/230
[58] Field of Search ............... 564/230; 558/419; 544/59, 106, 386; 546/153, 190; 514/227.5; 540/451

[56] References Cited

U.S. PATENT DOCUMENTS

| | | | |
|---|---|---|---|
| Re. 31,244 | 5/1983 | Petersen | 514/349 |
| 3,976,643 | 8/1976 | Diamond et al. | 558/419 |
| 4,057,636 | 11/1977 | Petersen | 514/609 |
| 4,491,595 | 1/1985 | Niemers et al. | 558/419 |

FOREIGN PATENT DOCUMENTS

| | | |
|---|---|---|
| 0150937 | 7/1985 | European Pat. Off. |
| 0195731 | 1/1987 | European Pat. Off. |
| 0271271 | 6/1988 | European Pat. Off. |

OTHER PUBLICATIONS

S. D. Longman et al., Pharmacology, vol. 110, 1989, p. 45 (110:530n).
Petersen et al., "Synthesis and Hypotensive Activity of N-Alkyl-N″-Cyano-N′-Pyridylguanidines", Journal of Medicinal Chemistry, 1978, vol. 21, No. 8.
E. T. Hansen & H. J. Petersen, "Synthesis of N-Alkyl-N-Cyano-4-Pyridylguanidines from 4-Pyridylthiocarbamic Acid via N-Alkyl-N′-Pyridylthioureas, or via 4-Pyridylthioureas, or via 4-Pyridylcyaniminothiocarbamic Acid", Synthetic Comm., 14(13), 1275–1283 (1983).
P. Siegl et al., "Effects of ATP-Sensitive Potassium Channel Modulators Glyburide and BRL 34915 on Ischemia-Induced Fibrillation in Isolated Rat Heats", FASEB Journal, vol. 3, A3607 (1989).
Nigel Cook, "The Pharmacology of Potassium Channels and Their Therapeutic Potential", TIPS, vol. 9, p. 21–28, (1988).
M. Bacaner et al., "Potassium Channel Blockage: A Mechanism for Suppressing Ventricular Fibrillation", Proc. Nat'l Acad. Sci., U. S. A., vol. 83, 2223–2227. Med. Sciences (1986).
M. J. Kerr et al., "Suppression of Ventricular Arrhythmias After Coronary Artery Ligation by Pinacidil, A Vasodilator Drug", J. Card. Pharm., vol. 7, 875–883 (1985).

Primary Examiner—Mukund J. Shah
Assistant Examiner—Edward C. Ward
Attorney, Agent, or Firm—Theodore R. Furman, Jr.

[57] ABSTRACT

Novel compounds of the formula

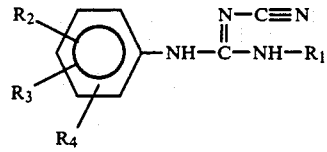

and tautomers thereof, wherein at least one of $R_2$, $R_3$ and $R_4$ is a strong electron withdrawing group, are disclosed. These compounds possess potassium channel activating activity and, as such, are useful as antihypertensive agents. Advantageously, the compounds of the present invention have shown less cardiac effects than known potassium channel activators.

Also disclosed is a process for preparing these and other compounds.

36 Claims, 2 Drawing Sheets

The Effect of Intracoronary Pinacidil (0.9 µg/kg/min) or Cromakalim (0.1 µg/kg/min) on Hemodynamic Variables Before and After LCX Occlusion in Anesthetized Dogs

| | Preocclusion | | Occlusion | Min Post-Reperfusion | | | | |
|---|---|---|---|---|---|---|---|---|
| | Pre Drug | Post Drug | 40 min Post Occlusion | 60 | 120 | 180 | 240 | 300 |
| Mean Aortic Pressure (mmHg) | | | | | | | | |
| Vehicle (n=9) | 112±6 | 104±5 | 97±8 | 88±6[a] | 93±9 | 92±7 | 91±8 | 91±7 |
| Pinacidil (n=6) | 126±5 | 113±6 | 105±8 | 99±8 | 101±8 | 100±7 | 100±7 | 100±8 |
| Cromakalim (n=6) | 124±7 | 120±7 | 116±4 | 114±6 | 114±6 | 107±6 | 107±6 | 110±8 |
| Heart Rate (beats/min) | | | | | | | | |
| Vehicle (n=9) | 143±5±5 | 140±7 | 138±5 | 155±6 | 147±8 | 143±5 | 152±5 | 155±6 |
| Pinacidil (n=6) | 148±13 | 152±15 | 156±14 | 136±9 | 142±11 | 144±12 | 147±14 | 152±11 |
| Cromakalim (n=6) | 152±6 | 152±7 | 156±5 | 153±7 | 155±6 | 162±4 | 164±4 | 168±4 |
| Ectopic Beats (beats/min) | | | | | | | | |
| Vehicle (n=9) | 0 | 0 | 0 | 61±19 | 48±16 | 78±21 | 124±22 | 116±2 |
| Pinacidil (n=6) | 0 | 0 | 0 | 10±5[b] | 38±29 | 55±31 | 59±30 | 154±12 |
| Cromakalim (n=6) | 0 | 0 | 0 | 33±20 | 23±22 | 28±26 | 29±26[b] | 50±27 |

All values are mean ± SE
[a] Significantly different from its respective predrug value (p>0.05)
[b] Significantly different from its respective vehicle group value (p>0.05)

FIG. 1

The Effect of Intracoronary Pinancidil (0.9 µg/kg/min) or Cromakalim (0.1 µg/kg/min) on Hemodynamic Variables Before and After LCX Occlusion in Anesthetized Dogs

| | Preocclusion | | Occlusion | Min Post-Reperfusion | | | | |
|---|---|---|---|---|---|---|---|---|
| | Pre Drug | Post-Drug | 40 min Post Occlusion | 60 | 120 | 180 | 240 | 300 |
| Mean Aortic Pressure (mmHg) | | | | | | | | |
| Vehicle (n=9) | 112±6 | 104±8 | 97±8 | 88±6[a] | 93±9 | 92±7 | 91±8 | 91±7 |
| Pinacidil (n=6) | 126±5 | 113±6 | 105±8 | 99±8 | 101±8 | 100±7 | 100±7 | 100±8 |
| Cromakalim (n=6) | 124±7 | 120±7 | 116±4 | 114±6 | 114±6 | 107±6 | 107±6 | 110±8 |
| Heart Rate (beats/min) | | | | | | | | |
| Vehicle (n=9) | 143±5±5 | 140±7 | 138±5 | 155±6 | 147±8 | 143±5 | 152±5 | 155±6 |
| Pinacidil (n=6) | 148±13 | 152±15 | 156±14 | 136±9 | 142±11 | 144±12 | 147±14 | 152±11 |
| Cromakalim (n=6) | 152±6 | 152±7 | 156±5 | 153±7 | 155±6 | 162±4 | 164±5 | 168±4 |
| Ectopic Beats (beats/min) | | | | | | | | |
| Vehicle (n=9) | 0 | 0 | 0 | 61±19 | 48±16 | 78±21 | 124±22 | 116±2 |
| Pinacidil (n=6) | 0 | 0 | 0 | 10±5[b] | 38±29 | 55±31 | 59±30 | 154±12 |
| Cromakalim (n=6) | 0 | 0 | 0 | 33±20 | 23±22 | 28±26 | 29±26[b] | 50±27 |

All values are mean ± SE

[a] Significantly different from its respective predrug value (p>0.05)
[b] Significantly different from its respective vehicle group value (p>0.05)

FIG. 2

The effect of intracoronary pinacidil (0.9 μg/kg/min) or cromakalim (0.1 μg/kg/min) on infarct size as a percent of the left ventricular (LV) area at risk

FIG. 3

The Effect of Intracoronary Pinacidil (0.9 μg/kg/min) or Cromakalim (0.1 μg/kg/min) on the Number of Fibrillations During Reperfusion

|  | Total Animals | Animals Fibrillated | % Fibrillation |
| --- | --- | --- | --- |
| Vehicle (n=9) | 9 | 7 | 78 |
| Pinacidil (n=6) | 6 | 1 | 17[a] |
| Cromakalim (n=6) | 6 | 1 | 17[a] |

[a] Significantly different from vehicle

ARYL CYANOGUANIDINES: POTASSIUM CHANNEL ACTIVATORS AND METHOD OF MAKING SAME

This is a continuation-in-part of U.S. Ser. No. 230,209, filed Aug. 9, 1988 now abandoned.

FIELD OF THE INVENTION

The present invention relates to novel compounds having potassium channel activating activity which are therefore, useful in the treatment of hypertension, and is additionally concerned with a method for preparing these and other compounds and a method of using potassium channel activators as antifibrillatory agents.

BACKGROUND OF THE INVENTION

Ischemia of the heart is the reduction of blood flow to cardiac tissue which can result in dysrhythmic conditions, e.g. ventricular arrhythmia and ventricular fibrillation, and cell death. Such dysrhythmic conditions are the result of the asynchronous excitability states created between normal and ischemic-injured cardiac cells which, in turn, caused a disruption of the normal ion transport channels within the cardiac tissue.

Ventricular fibrillation is generally considered to be a severe extension of less harmful ventricular arrhythmias. Arrhythmia rises to the level of fibrillation when this disruption results in action potential and conduction inhomogeneities that critically desynchronize normal excitation and contraction coupling over a sufficient portion of the heart (Bacaner et al., "Potassium Channel Blockade: A Mechanism for Suppressing Ventricular Fibrillation", *Proc. Nat'l. Acad. Sci. U.S.A.*, Vol. 83:2223-2227, April 1986:Medical Sciences).

However, despite the apparent link between arrhythmia and fibrillation, it has been found that lidocaine and procainamide, Class I antiarrhythmic agents, do not have antifibrillatory activity. These agents prevent ventricular arrhythmias but are unable to suppress ventricular fibrillation as disclosed by N. Cook, "The Pharmacology of Potassium Channels and Their Therapeutic Potential", TIPS, January 1988; Vol. 9: p. 21-28.

It is also interesting to note that similar results have been observed with certain anti-ischemic agents. For example, certain calcium channel blockers and thromboxane receptor antagonists have been identified as capable of significantly reducing infarct size and thus are potentially useful as anti-ischemic agents. Surprisingly, reduction of infarct size, accomplished via reperfusion (restoration of blood flow to previously injured cardiac tissue), does not dictate suppression of fibrillation. Likewise, reperfusion can be provided to an ischemic heart by various new surgical (bypass), mechanical (angioplasty) and thrombolytic means in a sufficiently timely fashion so as to save much of the ischemia-injured tissue.

The Bacaner et al. report further discloses that bretylium and bethanidine have been found useful in decreasing conduction inhomogeneities in the ischemic-injured heart resulting in an increase in action potential duration and decreased fibrillation. This antifibrillatory action is attributed to blockade of one or more of the potassium channels in the cells of the heart. Thus, potassium channel blockers are expected as a class to be useful as antifibrillatory agents. In fact, P. Siegl, et al., "Effects of ATP-Sensitive Potassium Channel Modulators, Glyburide and BRL 34915, on Ischemia-Induced Fibrillation in Isolated Rat Hearts", FASEB Journal, Vol. 3, #3, A3607 (1989), have observed profibrillatory activity for potassium channel activators such as pinacidil and BRL 34915 (cromakalim).

Petersen, in U.S. Pat. No. 4,057,636, discloses compounds of the formula wherein $R_2$ can be hydrogen, halogen, hydroxy, lower alkyl or lower alkoxy. These compounds are stated to be useful as antihypertensive agents.

Petersen et al., in "Synthesis and Hypotensive Activity of N-Alkyl-N''-Cyano-N'-Pyridylguanidines", Journal of Medicinal Chemistry, 1978, Vol. 21, No. 8, disclose compounds as above in U.S. Pat. No. 4,057,636 but wherein the pyridyl group has been replaced by a phenyl ring. Petersen et al. further disclose that such phenyl compounds are either inactive or only weakly active as antihypertensive agents.

SUMMARY OF THE INVENTION

In accordance with the present invention novel compounds having potassium channel activating activity which are therefore useful, for example, as antihypertensive agents, are disclosed. Advantageously, the compounds of the present invention have shown less cardiac effects than known potassium channel activators. These compounds have the general formula

Ia and its possible tautomers

Ib and

Ic including pharmaceutically acceptable salts
wherein $R_1$ is alkyl, alkenyl, alkynyl, haloalkyl, cycloalkyl, aryl, arylalkyl or cycloalkylalkyl;

-continued

$R_3$ and $R_4$ are each independently selected from —$R_2$, hydrogen, alkyl, alkenyl, alkynyl, haloalkyl, halo, alkoxy, —NHalkyl, —N—(alkyl)$_2$, —S—alkyl, —O—arylalkyl, —S—arylalkyl or —S—aryl, —O—aryl, —NHarylalkyl, or $R_2$ and $R_3$ taken together are a group which forms a ring with the two carbon atoms to which they are attached, which group is selected from wherein
m=1 or 2,
n=3-5,
p=2-4,
X is O, NR$_5$, CH$_2$; and
R$_5$ is hydrogen or R$_1$.

Also disclosed is an improved method for preparing compounds of formula I and other compounds all of which can be defined by the formula including tautomer forms thereof. Finally, the present invention discloses a method of using potassium channel activators as antifibrillatory agents.

DETAILED DESCRIPTION OF THE PRESENT INVENTION

In accordance with the present invention, it has been found that the compounds of formula I, having a phenyl group instead of the pyridyl group of the prior art are highly active hypotensive agents provided that one of the substituents on the phenyl ring is a strong electron withdrawing radical. Hence, the R$_2$ group of present formula I defines such a group of strongly electron withdrawing radicals.

This invention relates to the cyanoguanidine compounds of formula I above, to compositions and the method of using such compounds as cardio-vascular agents.

It has also been found that compounds of the present invention, and potassium channel activators in general, are useful as antifibrillatory agents.

The term lower alkyl used in defining various symbols refers to straight or branched chain saturated hydrocarbon radicals having up to eight carbons, preferably from one to five carbons. Similarly, the terms lower alkoxy and lower alkylthio refer to such lower alkyl groups attached to an oxygen or sulfur.

The term lower alkenyl refers to straight or branched chain hydrocarbon radicals having from two to eight carbons and one double bond, preferably three to five carbons. The term lower alkynyl refers to straight or branched chain hydrocarbon radicals having from two to eight carbons and one triple bond, preferably three to five carbons.

The term cycloalkyl refers to saturated carbocyclic rings of 4 to 7 carbon atoms with cyclopentyl and cyclohexyl being mos preferred.

The term halo refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl or mono substituted phenyl, wherein said substituent is lower alkyl of 1 to 4 carbons, lower alkylthio of 1 to 4 carbons, lower alkoxy of 1 to 4 carbons, halo, nitro, cyano, hydroxy, amino, —NH—alkyl wherein alkyl is of 1 to 4 carbons, —N(alkyl)$_2$ wherein alkyl is of 1 to 4 carbons, (wherein R$_6$ is hydrogen, lower alkyl of 1 to 4 carbons, lower alkoxy of 1 to 4 carbons, lower alkylthio of 1 to 4 carbons, halo, hydroxy or CF$_3$), —O—CH$_2$—cycloalkyl, or —S—CH$_2$—cycloalkyl, and di-substituted phenyl, wherein said substituents are selected from methyl, methoxy, methylthio, halo, CF$_3$, nitro, amino, and OCHF$_2$.

The term "substituted amino" refers to a group of the formula —NZ$_1$Z$_2$ wherein Z$_1$ is hydrogen, alkyl, cycloalkyl, aryl, arylalkyl, cycloalkylalkyl and Z$_2$ is alkyl, cycloalkyl, aryl, arylalkyl, cycloalkylalkyl or Z$_1$ and Z$_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl substituted with alkyl, alkoxy, alkylthio, halo, trifluoromethyl or hydroxy.

To prepare the compounds of formula I, first, an isothiocyanate of the formula can be reacted with cyanamide of the formula $$M^+NH-C\equiv N \qquad III$$

(wherein M is an alkali metal, e.g., sodium) in the presence of a solvent, such as ethanol, to provide a compound of the formula The thiourea of formula IV is thereafter reacted with an alkylating agent, such as dimethyl sulfate or methyl iodide, in the presence of one or more solvents, such as dimethylformamide, tetrahydrofuran or dioxane, to provide a compound of the formula or the tautomeric form thereof Reaction of compound Va or Vb with a compound of the formula

$$NH_2-R_1 \qquad VI$$

in a solvent, such as isopropanol, provides the compounds of formula I.

Alternatively, the compounds of formula I, as well as other compounds, can be prepared by a novel process which is part of the present invention. Compounds which can be prepared by this novel process are defined by the formula and the tautomeric forms and wherein R' and R" are each independently selected from alkyl, phenyl, pyridyl, phenylalkyl, alkenyl, alkynyl, haloalkyl, cycloalkyl, arylalkyl, cycloalkylalkyl, and wherein $R_2$, $R_3$ and $R_4$ are as defined above.

The process for making compounds of formula VII (and thereby compounds of formula I) involves treating a compound of the formula $$R'-N=C=S \qquad VIII$$

in the same manner as compound II above to provide a compound of the formula

The present process utilizes a carbodiimide of the formula wherein $R_6$, $R_7$ and $R_8$ are alkyl, cycloalkyl, phenyl, phenylalkyl, cycloalkylalkyl and $R_6$ and $R_7$ taken together with the nitrogen atom to which they are attached are 1-pyrrolidinyl, 1-piperidinyl, 4-morpholinyl, 4-thiomorpholinyl, 4-alkyl-1-piperazinyl, 4-phenylalkyl-1-piperazinyl and x is halo. Reaction of compound IX with a compound of formula X and an amine of formula R"NH$_2$, in a polar solvent, such as dimethylformamide, provides the corresponding compounds of formula VII (and thereby compounds of formula I).

Compounds of formula VII can also be prepared without isolating the intermediates of formula IX by reacting a compound of formula VIII with a compound of formula III in a solvent, such as ethanol, followed by treatment with compound X and an amine of formula R"NH$_2$, as described above.

Preparation of analogs of compound VII is known using dicyclohexylcarbodiimide but this reaction takes 6-7 days to complete. (See "Synthesis of N-Alkyl-N-Cyano-4-Pyridylguanidines From 4-Pyridylthiocarbamic Acid via N-Alkyl-N'-4-Pyridylthioureas, or via 4-Pyridylcyaniminothiocarbamic Acid", E. T. Hansen and H. J. Peterson, Synthetic Communications, 14(13), 1275-1283 (1984)). While compounds of the present invention have been made using the above described process, it took 7 days to achieve yields of less than 5%. Alternate prior art processes offer some improvement, but still take 1-2 days to provide yields in the 20% range. The novel process of the present invention provides a dramatic enhancement in the rate of the reaction and gives high yields of compounds of formula VII as will be more clearly illustrated in the examples.

If any of $R_1$, $R_2$, $R_3$, $R_4$ and $R_5$ in the above reactions are aryl or arylalkyl wherein aryl is phenyl substituted with one hydroxy or one or more amino groups, or a substituted alkyl such as hydroxylalkyl, aminoalkyl or mercaptoalkyl, then the hydroxyl, amino, or mercaptan function should be protected during the reaction. Suitable protecting groups include benzyloxycarbonyl, t-butoxycarbonyl, benzyl, benzhydryl, etc. The protecting group is removed by hydrogenation, treatment with acid, or by other known means following completion of the reaction.

Preferred compounds of this invention are those wherein:
$R_1$ is alkyl, cycloalkyl or cycloalkyalkyl;
$R_2$ is —C≡N, $NO_2$, $CF_3$, $R_3$ $R_4$ are independently selected from hydrogen, alkyl, or alkoxy.

Most preferred compounds of this invention are those wherein:
$R_1$ is t-butyl, t-pentyl or sec-3,3-dimethylbutyl;
$R_2$ is C≡N; and
$R_3$ and $R_4$ are H.

The compounds of formula I form salts with a variety of inorganic and organic acids. The non-toxic pharmaceutically acceptable salts are preferred, although other salts may also be useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

In addition, the compounds of formula I in which $R_2$-$R_4$ is include carboxylic acid salts, i.e., $R_5$ is a pharmaceutically acceptable salt forming ion. Preferred salt forming ions include alkali metal salt ions such as sodium, potassium, and lithium, and alkaline earth metal salt ions such as calcium and magnesium.

The compounds of formula I and the pharmaceutically acceptable salts thereof are useful as cardiovascular agents. These compounds act as potassium channel activators and are especially useful as antihypertensive agents. Thus, by the administration of a composition containing one (or a combination) of the compounds of this invention the blood pressure of a hypertensive mammalian (e.g., human) host is reduced. A single dose, or preferably two to four divided daily doses, provided on a basis of about 0.001 to 100 mg per kilogram of body weight per day, preferably from about 0.1 to about 25 mg per kilogram per day, is appropriate to reduce blood pressure. The substance is preferably administered orally, but parenteral routes, such as the subcutaneous, intramuscular, intravenous, transdermal routes or any other convenient delivery system can also be employed.

As a result of the potassium channel activating activity of compounds of this invention, these compounds are also useful in the treatment of cardiovascular disorders and any disorders associated with smooth muscle contraction. For example, compounds of the present invention which act as potassium channel activators are useful as therapy for congestive heart failure, therapy for peripheral vascular disorders (e.g. Raynaud's Disease), therapy for pulmonary hypertension, as anti-ischemic agents, as anti-anginal agents, as anti-fibrillatory agents, as thrombolytic agents and in limiting myocardial infarction.

Compounds of the present invention are additionally expected to be useful in the treatment of central nervous system disorders (e.g., Parkinsonism, as anti-tremor agents, epilepsy), in therapy for renal failure, in therapy for urinary incontinence, as anti-diarrheal agents, in therapy for pre-eclampsia, dysmenorrhea and premature labor, as well as for the promotion of hair growth (e.g., in the treatment of male pattern baldness) and as anti-asthmatic agents.

The compounds of this invention can also be formulated in combination with digitalis (for heart failure patients), with a diuretic such as, chlorothiazide, hydrochlorothiazide, flumethiazide, hydroflumethiazide, bendroflumethiazide, methylchlothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), calcium channel blocking agents such as nifedipine or diltiazem, β-blockers or antiarrhythmic agents. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 0.02 to 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Additionally, the compounds of the present invention have advantageously been found to have less cardiac effects than known potassium channel activators. For example, decreased effects on cardiac electrical activity (e.g., action potential duration) have been observed in comparisons of compounds of the present invention to prior art compounds, e.g., pinacidil, which has the chemical formula As mentioned above, the present invention further encompasses the use of potassium channel activators as antifibrillatory agents. This is unexpected since the prior art, as described above, predicts that potassium channel blockers are antifibrillatory and, in fact, that certain potassium channel activators have pro-fibrillatory tendencies. Surprisingly, it has been found that potassium channel activators are useful as antifibrillatory agents. Therefore the present method comprises preventing or treating fibrillation of the heart in a mammalian species by the administration of a therapeutically effective amount of one or more potassium channel activators. In a preferred embodiment this novel method comprises administering potassium channel activators prior to or during reperfusion, it being understood that such reperfusion can be the result of occlusion removal (e.g., by surgical, angioplasty or thrombolytic means) and/or from treatment with anti-ischemic agents.

Further, since it is now known that potassium channel activators are also useful as anti-ischemic agents, as has been disclosed in U.S. Ser. No. 220,866 (HA474), concurrent ischemia and fibrillation can be treated by the administration of potassium channel activators.

Examples of potassium channel activators include (+)-2-cyano-1-(4-pyridyl)-3-(1,2,2-trimethylpropyl)-guanidine (hereinafter referred to as pinacidil) and (±)-6-cyano-3,4-dihydro-2,2-dimethyl-trans-4-(2-oxo-1-pyrrolidyl)-2H-benzo[b]-pyran-3-ol (hereinafter referred to as cromakalim or BRL 34915).

Other examples of compounds which are potassium channel activators but which have substantially weaker PCA activity include N-(2-hydroxyethyl)nicotinamide nitrate ester (hereinafter referred to as nicroandil) and 6-amino-1,2-dihydro-1-hydroxy-2-imino-4-piperidinopyrimidine (hereinafter referred to as minoxidil).

In carrying out the method of the present invention, the potassium channel activator may be administered to mammalian species, such as monkeys, dogs, cats, rats, humans, etc., during the period of fibrillation and/or prior to or during the period of reperfusion and/or shortly after termination of an ischemic attack, for example, within 1 to 2 hours after the ischemia.

Although the potassium channel activator may be administered systemically, such as orally or parenterally, it is preferred that the potassium channel activator be administered locally to the coronary arteries by catheter such as by arterial angiography or intracoronary injection.

With regard to dosage of potassium channel activator, where the drug is administered by arterial angiography or intracoronary injection, from about 0.001 to about 30 mg/kg/treatment and preferably from about 0.5 to about 25 mg/kg/treatment will be employed. The number of treatments will depend upon the severity of the fibrillation and the progress of reperfusion to achieve normal heart rhythm. Usually, from 1 to 5 treatments per day will be required for as long as fibrillation continues.

Where the potassium channel activator is to be administered by angiography or intracoronary injection, it will be formulated in a conventional vehicle, such as distilled water, saline, Ringer's solution, or other conventional carriers.

The potassium channel activator may also be incorporated in a conventional dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms are quite satisfactory as well.

With regard to such systemic formulations, single or divided doses of from about 5 to about 2,500 mg, preferably from about 10 to 2,000 mg/one to four times daily, may be administered in systemic dosage forms as described above for a period sufficient to restore normal heart function.

The present invention will be further illustrated by the following examples but should not be limited to the details described therein.

EXAMPLE 1

4-[[(Cyanoimino)[(1,2,2-trimethylpropyl)-amino]methyl]amino]benzonitrile

A. N-Cyano-N'-(4-cyanophenyl)thiourea

A suspension of 4-cyanophenyl isothiocyanate (10.75 g, 67.2 mmol) and monosodium cyanamide (4.30 g, 67.2 mmol) in absolute ethanol (35 ml) was heated at 90° C. (oil bath) for 3.0 hours under argon. The reaction was then cooled (ice bath) and filtered to give the title A compound as a gray-white solid (9.92 g), m.p.>230° C. TLC (10% MeOH/CH$_2$Cl$_2$) single spot, R$_f$=0.08.

B. N-Cyano-N'-(4-cyanophenyl)carbamidothioic acid methyl ester, methylsulfate

A suspension of thiourea of the title A compound (9.00 g, 44.5 mmol) in tetrahydrofuran/ dimethylformamide (44 ml each) was treated with dimethyl sulfate (4.43 ml, 46.7 mmol) dropwise over five minutes under argon. Within a few minutes the suspension became a clear solution. After stirring overnight, the reaction was partially evaporated and diluted with ether. The solids which precipitated were filtered to give the title B compound as a white solid (11.45 g), m.p. 194–202° C. TLC (10% MeOH/CH$_2$Cl$_2$) single spot, R$_f$=0.41.

C. 4-[[(Cyanoimino)[(1,2,2-trimethylpropyl) -amino]-methyl]amino]benzonitrile

A mixture of the title B compound (11.40 g, 40.8 mmol) and 2-amino-3,3-dimethyl butane (13.7 ml, 102 mmol) in isopropanol (82 ml) was heated at 90° C. (oil bath) under argon overnight. The reaction was then cooled and evaporated. The residue was partitioned between ethyl acetate and 10% citric acid solution. The organic phase was washed with water, saturated sodium chloride, dried over anhydrous magnesium sulfate, and evaporated. Flash chromatography of the residue (9.32 g) over Merck silica (1000 ml) eluting with 30% acetone/ hexane gave a white solid (3 g). Crystallization from isopropanol (twice) gave the title compound as free-flowing, white crystals (1.15 g), m.p. 191–192° C. TLC (40% Acetone/Hexane) single spot, R$_f$=0.41. TLC (15% EtOAc/CH$_2$Cl$_2$) single spot, R$_f$=0.15.

Microanalysis for C$_{15}$H$_{19}$N$_5$:

Calc'd: C, 66.88; H, 7.11; N, 26.01;

Found: C, 66.86; H, 7.30; N, 25.90.

EXAMPLE 2

N''-Cyano-N-(4-nitrophenyl)-N'-(1,2,2-trimethylpropyl)guanidine

A. N-Cyano-N'-(4-nitrophenyl)thiourea

A suspension of 4-nitrophenyl isothiocyanate (10.0 g, 55.5 mmol) and monosodium cyanamide (3.55 g, 55.5 mmol) in absolute ethanol (30 ml) was heated at 90° C. (oil bath) for 3.0 hours under argon. The reaction was then cooled (ice bath) and filtered to give a yellow solid (7.4 g), m.p. >230° C. TLC (10% MeOH/CH$_2$Cl$_2$) single spot, R$_f$=0.08.

B. N-Cyano-N'-(4-nitrophenyl)carbamidothioic acid, methyl ester, methyl sulfate

A suspension of thiourea of the title A compound (6.3 g, 28.35 mmol) in dimethylformamide (15 ml) was treated with dimethyl sulfate (2.8 ml, 29.8 mmol) dropwise over five minutes under argon. Within a few minutes the suspension became a clear solution. After stirring overnight, the reaction was diluted with ether. The solids which precipitated were filtered to give the title B compound (8.68 g) as a white solid, m.p. 165–167° C. TLC (40% acetone/hexanes) single spot, R$_f$=0.25.

C. N''-Cyano-N-(4-nitrophenyl)-N'-(1,2,2-trimethylpropyl)guanidine

A mixture of title B compound (8.5 g, 25.8 mmol) and 2-amino-3,3-dimethyl butane (10.4 ml, 77.4 mmol) in isopropanol (80 ml) was heated at 90° C. (oil bath) under argon overnight. The reaction was then cooled and evaporated. The residue was partitioned between ethyl acetate and 10% citric acid solution. The organic phase was washed with water, saturated sodium chloride, dried over anhydrous magnesium sulfate, and evaporated. Flash chromatography of the residue (9.32 g) over Merck silica gel eluting with 20% acetone/hexane gave a yellow solid. Crystallization from isopropanol gave the desired product as a yellow solid (1.12 g), m.p. 211–212° C. TLC (40% Acetone/Hexane) single spot, R$_f$=0.4.

Microanalysis for C$_{14}$H$_{19}$N$_5$O$_2$:
Calc'd: 58.11; H, 6.62; N, 24.21;
Found: C, 58.01; H, 6.60; N, 24.04.

EXAMPLE 3

N''-Cyano-N-(3-nitrophenyl)-N'-(1,2,2-trimethylpropyl)guanidine

A. N-Cyano-N'-(3-nitrophenyl)thiourea

A suspension of 4-nitrophenyl isothiocyanate (10.0 g, 55.5 mmol) and monosodium cyanamide (3.55 g, 55.5 mmol) in absolute ethanol (30 ml) was heated at 90° C. (oil bath) for 3.0 hours under argon. The reaction was then cooled (ice bath) and filtered to give a yellow solid (10.2 g), m.p. >210° C.

B. N-Cyano-N'-(3-nitrophenyl)carbamidothioic acid, methyl ester, methyl sulfate

A suspension of thiourea of the title A compound (9.6 g, 43.2 mmol) in dimethylformamide (25 ml) was treated with dimethyl sulfate (4.3 ml, 45.3 mmol) dropwise over five minutes under argon. Within a few minutes the suspension became a clear solution. After stirring overnight, the reaction was diluted with ether. The solids which precipitated were filtered to give the title B compound (16.07 g) as a white solid, m.p. >210° C. (softens at 152° C.). TLC (40% acetone/hexanes) single spot, R$_f$=0.1.

C. N''-Cyano-N-(3-nitrophenyl)-N'-(1,2,2-trimethylpropyl)guanidine

A mixture of the title B compound (16.0 g, 43.2 mmol) and 2-amino-3,3-dimethyl butane (17.4 ml, 129.6 mmol) in isopropanol (45 ml) was heated for 6 hours at 90° C. (oil bath) under argon. The reaction was then cooled and evaporated. The residue was partitioned between ethyl acetate and 10% citric acid solution. The organic phase was washed with water, saturated sodium chloride, dried over anhydrous magnesium sulfate, and evaporated. The residue was purified by flash chromatography (5–25% ethyl acetate in dichloromethane) to yield a yellow solid. It was crystallized from isopropanol to give the desired product as a colorless solid (0.98 g), m.p. 183–184° C. TLC (35% Acetone/Hexane) single spot, R$_f$=0.25.

Microanalysis for C$_{14}$H$_{19}$N$_5$O$_2$:
Calc'd: C, 58.11; H, 6.62; N, 24.21;
Found: C, 58.05; H, 6.72; N, 24.19.

The following examples illustrate the novel process of the present invention.

EXAMPLE 4

4-[[(Cyanoimino)[(2,2-trimethylpropyl)-amino]methyl]amino]benzonitrile

A mixture of the title A compound from Example 1 (404 mg, 2.0 mmol), diisopropylethylamine (0.4 mL) and 2-amino-3,3-dimethyl butane (0.35 ml, 2.4 mmol) in dimethylformamide (3 ml) at room temperature was treated with 1-(3-dimethylaminopropyl)-3-ethylcarbodiimide hydrochloride (400 mg, 2.3 mmol) and allowed to stir for 15 minutes. The reaction was then partitioned between 1N hydrochloric acid and ethyl acetate. The organic phase was washed with water and saturated sodium chloride solution, and dried over anhydrous magnesium sulfate. Evaporation and crystallization of the product from isopropanol gave a colorless solid (400 mg), m.p. 188–190° C.

TLC (40% Acetone/Hexane) single spot, R$_f$=0.42.
Microanalysis for C$_{15}$H$_{19}$N$_5$:
Calc'd: C, 66.88; H, 7.11; N, 26.01;
Found: C, 66.52; H, 7.10; N, 25.90.

EXAMPLE 5

N''-Cyano-N-(2-nitrophenyl)-N'-(1,2,2-trimethylpropyl)guanidine

A mixture of 2-nitrophenyl isothiocyanate (6.00 g, 33 mmol) and monosodium cyanamide (1.92 g, 30 mmol) in dioxane (15 ml) was heated at 85° C. (oil bath) overnight under argon. The reaction was then diluted with dimethylformamide (15 ml). Diisopropylethylamine (2.76 ml, 33 mmol) and 2-amino-3,3-dimethyl butane (2.36 ml, 33 mmol) were added, and the resulting mixture was treated with 1-(3-dimethylaminopropyl)-3-ethylcarbodiimide hydrochloride (7.68 g, 44 mmol). After stirring for 1 hour, the reaction was partitioned between ethyl acetate and 1N hydrochloric acid. The organic phase was washed with water (four times) and saturated sodium chloride solution, dried over anhydrous magnesium sulfate, and evaporated. The crude product was flash chromatographed (4% EtOAc/ CH$_2$Cl$_2$) over Merck silica (650 g). The fractions containing the desired product were combined and evaporated to give the title compound as a yellow oil (4.96 g) which was crystallized to give free-flowing yellow crystals (2.31 g), m.p. 116–118° C. TLC (40% Acetone/Hexane) single spot, $R_f=0.33$. TLC (10% EtOAc/CH$_2$Cl$_2$) single spot, $R_f=0.49$.

Microanalysis for C$_{14}$H$_{19}$N$_5$O$_2$:
Calc'd: C, 58.11; H, 6.62; N, 24.21;
Found: C, 58.10; H, 6.55; N, 24.10.

EXAMPLE 6

3-[[(Cyanoimino)[(1,2,2-trimethylpropyl)-amino]methyl]amino]benzonitrile

A suspension of 3-cyanophenyl isothiocyanate (2.0 g, 12.48 mmol) and monosodium cyanamide (726 mg, 11.35 mmol) in absolute ethanol (10 ml) was heated at 100° C. (oil bath) overnight under argon. The reaction was then cooled to room temperature, diluted with dimethylformamide (11 mL) and treated with 2-amino-3,3-dimethylbutane (1.7 mL, 12.5 mmol) followed by 1-(3-dimethylaminopropyl)-3-ethylcarbodiimide hydrochloride (4.35 g, 22.7 mmol). The reaction was stirred at room temperature for 1 hour and partitioned between 1N hydrochloric acid and ethyl acetate. The organic phase was washed with water, saturated sodium chloride, dried over anhydrous magnesium sulfate, and evaporated. The residue, after evaporation of the solvent, was purified by flash chromatography over Merck silica gel (20% acetone in hexane) to give a colorless solid (890 mg). Crystallization from chloroformisopropyl ether gave the title compound as a colorless solid, m.p. 172-173° C. TLC (40% Acetone/ Hexane) single spot, $R_f=0.45$.

Microanalysis for C$_{15}$H$_{19}$N$_5$:
Calc'd: C, 66.8B; H, 7.11; N, 26.01;
Found: C, 66.54; H, 7.04; N, 25.75.

EXAMPLE 7

N''-Cyano-N-(4-cyanophenyl)-N'-(1-dimethylethyl)-guanidine

A solution of the title A compound from Example 1 (2.02 g, 10.0 mmol) and 1,1-dimethylethyl amine (1.26 mL, 12.0 mmol) in dimethylformamide (5 mL) was treated with 1-(3-dimethylaminopropyl)-3-ethylcarbodiimide hydrochloride (2.52 g, 13.0 mmol) at room temperature under argon. After 2 hours, the reaction was partitioned between ethyl acetate and water. The aqueous layer was reextracted with ethyl acetate, and combined extracts were washed with 1N HCl, water and brine. After drying over anhydrous magnesium sulfate, the solvent was evaporated and the residue was purified by flash chromatography on silica gel (30% acetone in hexanes) to yield a colorless solid (1.12). The product was recrystallized from acetonitrile to provide the title compound as a colorless solid, m.p. 184-185° C.

Analysis calc'd for C$_{13}$H$_{15}$N$_5$:
C, 64.71; H, 6.27; N, 29.02;
Found: C, 64.41; H, 6.21; N, 28.80.

EXAMPLE 8

N''-Cyano-N-(4-cyanophenyl)-N''-(1,1-dimethylpropyl)-guanidine

A solution of the title A compound from Example 1 (3.0 g, 14.8 mmol) and t-amyl amine (1.9 mL, 16.3 mmol) in dimethylformamide (15 mL) was treated with 1-(3-dimethylaminopropyl)-3-ethylcarbodiimide hydrochloride (3.4 g, 16.3 mmol) at room temperature under argon. After 45 minutes, the reaction was partitioned between ethyl acetate and water. The aqueous layer was reextracted with ethyl acetate, and combined extracts were washed with 1N HCl, water and brine. After drying over anhydrous magnesium sulfate, the solvent was evaporated and the residue was purified by flash chromatography on silica gel (5% ethyl acetate in dichloromethane). The resulting colorless solid (1.4 g) was recrystallized from isopropanolisopropyl ether to provide the title compound, m.p. 137-138° C.

Analysis calc'd for C$_{14}$H$_{17}$N$_5$:
C, 65.85; H, 6.71; N, 27.44;
Found: C, 65.68; H, 6.67; N, 27.12.

EXAMPLES 9-31

Employing the procedures of Examples 2 to 6 above, the following compounds within the scope of the present invention can be prepared.

EXAMPLE 9

N-Cyano-N'-(4-cyanophenyl)-N''-cyclohexylguanidine.

EXAMPLE 10

N-Cyano-N'-(4-cyanophenyl)-N''-(l-cyclohexylethyl)guanidine.

EXAMPLE 11

N-Cyano-N'-(4-cyanophenyl)-N''-(l-phenylethyl)-guanidine.

EXAMPLE 12

N-Cyano-N'-(4-cyanophenyl)-N''-(phenylmethyl)-guanidine.

EXAMPLE 13

N-Cyano-N'-[4-(trifluoromethyl)phenyl]-N''-(1,2,2-trimethylpropyl)guanidine.

EXAMPLE 14

N-(4-Acetylphenyl)-N'-cyano-N''-(1,2,2-trimethylpropyl)guanidine.

EXAMPLE 15

4-[[(Cyanoimino)[(1,2,2-trimethylpropyl)amino]methyl]amino]benzoic acid, ethyl ester.

EXAMPLE 16

4-[[(Cyanoimino)[(1,2,2-trimethylpropyl)amino]methyl]amino]-N-methylbenzamide.

EXAMPLE 17

4-[[(Cyanoimino)[(1,2,2-trimethylpropyl)amino]methyl]amino]-N-(phenylmethyl)benzamide.

EXAMPLE 18

4-[[(Cyanoimino)[(1,2,2-trimethylpropyl)amino]methyl]amino]-N,N-dimethylbenzamide.

EXAMPLE 19

N-Cyano-N'-[4-(1-piperidinylcarbonyl)phenyl]-N''-(1,2,2-trimethylpropyl)guanidine.

EXAMPLE 20

N-Cyano-N'-[4-(4-morpholinylcarbonyl)phenyl]-N''-(1,2,2-trimethylpropyl)guanidine.

EXAMPLE 21

N-Cyano-N'-[4-(4-thiomorpholinylcarbonyl)phenyl]-N''-(1,2,2-trimethylpropyl)guanidine.

EXAMPLE 22

N-Cyano-N'-[4-[[4-(phenylmethyl)-1-piperazinyl]carbonyl]phenyl]-N''-(1,2,2-trimethyl-propyl)guanidine.

EXAMPLE 23

N-Cyano-N'-(5,6,7,8-tetrahydro-5-oxo-2-naphthalenyl)-N''-(1,2,2-trimethylpropyl)guanidine.

EXAMPLE 24

N-Cyano-N'-(1,1-dimethylethyl)-N''-(1,2,3,4-tetrahydro-2-methyl-1-oxo-6-isoquinolinyl)guanidine.

EXAMPLE 25

N-Cyano-N'-(1,1-dimethylpropyl)-N''-[3-(methylsulfonyl)phenyl]guanidine.

EXAMPLE 26

N-Cyano-N'-(1,1-dimethylpropyl)-N''-3-(methylsulfinyl)phenyl]guanidine.

EXAMPLE 27

N-(3-Chloro-4-nitrophenyl)-N'-cyano-N''-(1,1-dimethylethyl)guanidine.

EXAMPLE 28

N-Cyano-N'-(4-fluoro-3-nitrophenyl)-N''-(1,1-dimethylethyl)guanidine.

EXAMPLE 29

N-Cyano-N'-(4-cyano-3-methoxyphenyl)-N''-(1,2,2-trimethylpropyl)guanidine.

EXAMPLE 30

N-(3-Chloro-4-cyanophenyl)-N'-cyano-N''-(1,1-dimethylethyl)guanidine.

EXAMPLE 31

N-Cyano-N'-(1-cyclohexylethyl)-N''-[2-(trifluoromethyl)phenyl]guanidine.

EXAMPLE 32

N-Cyano-N'-(4-cyanophenyl)-N''-(2-cyclohexyl-1-methylethyl)guanidine.

EXAMPLE 33

Mongrel dogs of either sex (10-17 kg) were anesthetized with intravenous sodium pentobarbital (30 mg/kg) and a catheter was placed into the right femoral artery for collection of blood samples. A Millar Mikrotip catheter pressure transducer was placed into the left femoral artery and was advanced into the aortic arch for the measurement of arterial blood pressure. An endotracheal tube was placed into the trachea and the animals were artificially respired such that eucapnia was maintained.

A left thoracotomy was performed at the fifth intercostal space and the heart was exposed. The LCX was isolated proximal to its first branch and a silk suture was placed around it for later occlusion. In all animals a bent 27 gauge needle with an attached catheter was inserted into the LCX distal to the occluder for intracoronary (i.c.) infusions of drug. A catheter was placed into the left atrial appendage for dye and radioactive microsphere injection.

The animals were allowed to stabilize for 5-10 minutes at which time an arterial blood sample was removed anaerobically for measurement of blood gases using a Radiometer (ABL3, Copenhagen) blood gas analyzer. Arterial blood pressure, heart rate and ECG were measure. All animals were subjected to LCX occlusion for 90 minutes. Before occlusion, the animals were divided into 3 groups: 1) Animals given pinacidil (0.9 µg/kg/min., i.c., n=6) starting 10 minutes before LCX occlusion. 2) Animals given cromakalim (0.1 µg/kg/min., i.c., n=6) starting 10 minutes before LCX occlusion. 3) Vehicle control animals for groups 1 and 2 (n=9). At 90 minutes after the initiation of occlusion, the LCX was reperfused. The reperfusion was continued for a total of 5 hours at which time the LCX was cannulated and perfused at the animals' existing pressure with Ringer's lactate for determination of the area at risk. Patent blue violet dye (1 mg/kg of a 10 mg/ml solution) was injected into the left atrial catheter and the heart was quickly excised.

The atria were trimmed away leaving only the ventricles. The ventricles were then cut transversely into 0.5 cm slices. The borders of the area at risk (no dye) were delineated and separated and the slices were incubated at 37° C. for 30 minutes in a 1% solution of 2,3,5-triphenyl tetrazolium chloride in phosphate buffered saline. The ventricular slices were then dried and both sides were carefully traced onto clear transparencies. The area at risk and the infarcted region were demarcated on the transparencies. These tracings were transferred to paper and the areas of interest were measured using planimetric techniques. The infarct size was expressed as a percent of the left ventricular (LV) area at risk.

The number of animals which fibrillated during reperfusion were enumerated in each group. No animals fibrillated during LCX occlusion. Ectopic beats were counted when the P wave was dissociated from the QRS complex.

Changes in hemodynamic, blood flow, and infarct size variables were analyzed using an analysis of variance. Multiple comparisons were done using the Newman-Keuls test. For the determination of differences in the frequency of animals fibrillating during reperfusion, the Fisher exact test was used. All values are expressed as mean±SE.

Figure 1:
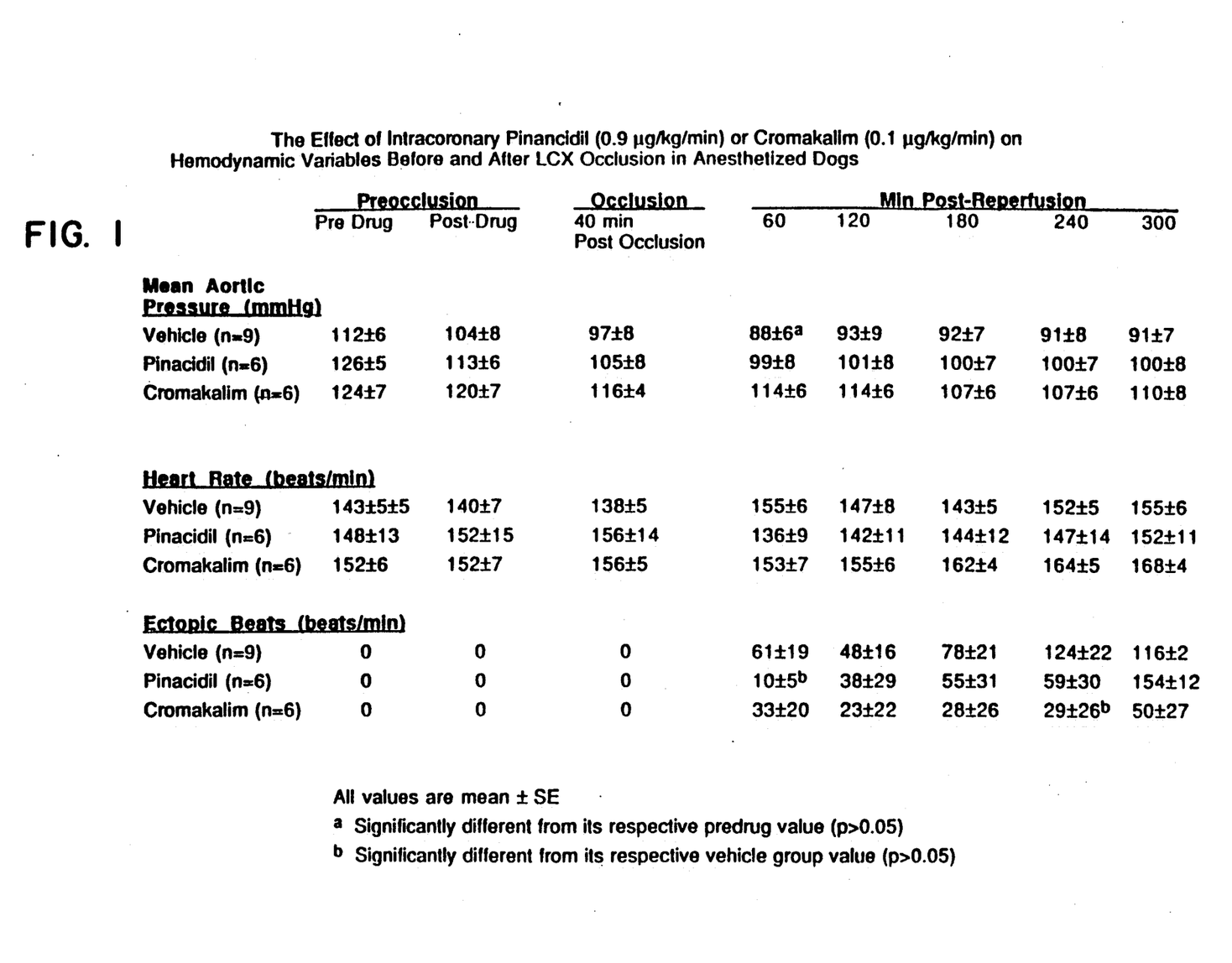
FIG. 1 is a table showing the effect of intracoronary pinancidil (0.9 μg/kg/min) or cromakalim (0.1 μg/kg/min) on hemodynamic variables before and after LCX occlusion in anesthetized dogs.
Figure 2:
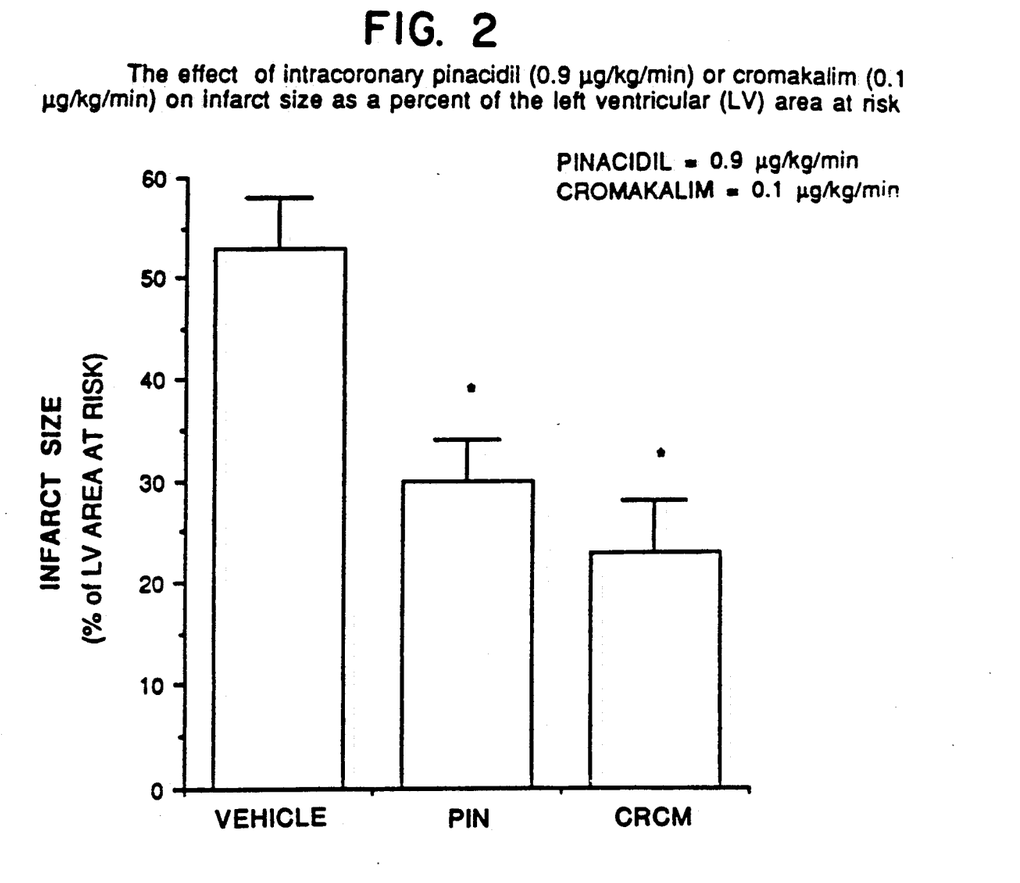
FIG. 2 is a graph showing the effect of intracoronary pinancidil (0.9 μg/kg/min) or cromakalim (0.1 μg/kg/min) on infarct size as a percent of the left ventricular (LV) area at risk.
Figure 3:
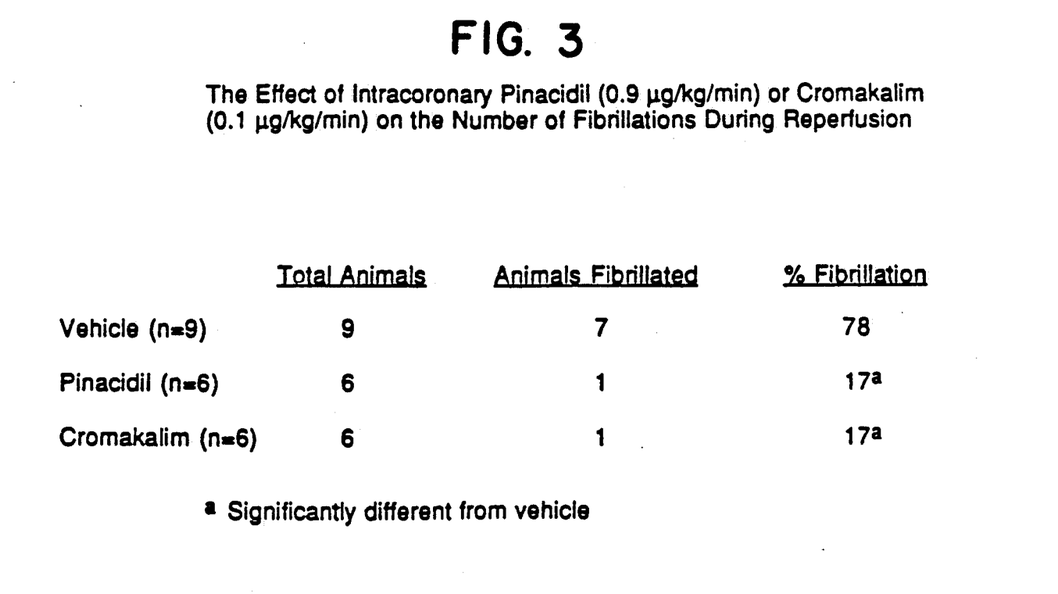
FIG. 3 is a table showing the effect of intracoronary pinancidil (0.9 μg/kg/min) or cromakalim (0.1 μg/kg/min) on the number of fibrillations during reperfusion.

As can be seen in Table 1 of FIG. 1, none of the drug treatments had a major effect on arterial blood pressure or heart rate. Despite the lack of hemodynamic effects, both pinacidil and cromakalim were observed to significantly reduce infarct size expressed as a percent of the area at risk (FIG. 2). The number of ectopic beats (number/minute) at various times during the reperfusion period are also shown on Table 1. At several times during the reperfusion, both cromakalim and pinacidil significantly reduced the frequency of ectopy. The frequency of reperfusion fibrillation in each respective treatment group is shown in Table 2 of FIG. 3. Seventy eight percent of vehicle treated animals fibrillated compared with seventeen percent in each of the drug treated groups. These differences were significant using the Fisher exact test.

What is claimed is:

1. Compounds having the formula and its possible tautomers and including pharmaceutically acceptable salts
wherein R₁ is alkyl, alkenyl, alkynyl, haloalkyl, cycloalkyl, aryl, arylalkyl or cycloalkylalkyl;

R₃ and R₄ are each independently selected from —R₂, hydrogen, alkyl, alkenyl, alkynyl, haloalkyl, halo, alkoxy, —NHalkyl, —N—(alkyl)₂, —S—alkyl, —O—arylalkyl, —S—arylalkyl or —S—aryl, —O—aryl, —NHarylalkyl.

2. A compound of claim 1 wherein
R₁ is alkyl, cycloalkyl or cycloalkylalkyl;
R₂ is —C≡N, NO₂, CF₃, R₃ and R₄ are independently selected from hydrogen, alkyl, or alkoxy.

3. A compound of claim 1 wherein
R₁ is t-butyl, t-pentyl or sec-3,3-dimethylbutyl;
R₂ is C≡N; and
R₃ and R₄ are H.

4. A compound of claim 1 having the name 4-[[(cyanoimino)[(1,2,2-trimethylpropyl)amino]methyl]amino]benzonitrile.

5. A compound of claim 1 having the name N''-cyano-N-(4-nitrophenyl)-N'-(1,2,2-trimethylpropyl)-guanidine.

6. A compound of claim 1 having the name N''-cyano-N-(3-nitrophenyl)-N'-(1,2,2-trimethylpropyl)-guanidine.

7. A compound of claim 1 having the name N''-cyano-N-(2-nitrophenyl)-N'-(1,2,2-trimethylpropyl)-guanidine.

8. A compound of claim 1 having the name 3-[[(Cyanoimino)[(1,2,2-trimethylpropyl)-amino]methyl]amino]benzonitrile.

9. A compound of claim 1 having the name N''-cyano-N-(4-cyanophenyl)-N'-(1,1-dimethylethyl)-guanidine.

10. A compound of claim 1 having the name N''-cyano-N-(4-cyanophenyl)-N'-(1,1-dimethylpropyl)-guanidine.

11. A compound of claim 1 having the name N-cyano-N'-(4-cyanophenyl)-N''-cyclohexylguanidine.

12. A compound of claim 1 having the name N-cyano-N'-(4-cyanophenyl)-N''-(1-cyclohexylethyl)-guanidine.

13. A compound of claim 1 having the name N-cyano-N'-(4-cyanophenyl)-N''-(1-phenylethyl)guanidine.

14. A compound of claim 1 having the name N-cyano-N'-(4-Cyanophenyl)-N''-(phenylmethyl)guanidine.

15. A compound of claim 1 having the name N-cyano-N'-[4-(trifluoromethyl)phenyl]-N''-(1,2,2trimethylpropyl)guanidine.

16. A compound of claim 1 having the name N-(4-acetylphenyl)-N'-cyano-N''-(1,2,2-trimethylpropyl)-guanidine.

17. A compound of claim 1 having the name 4-[[(cyanoimino)[(1,2,2-trimethylpropyl)amino]methylamino]benzoic acid, ethyl ester.

18. A compound of claim 1 having the name 4-[[(cyanoimino)[(1,2,2-trimethylpropyl)amino]methyl]amino]-N-methylbenzamide.

19. A compound of claim 1 having the name 4-[[(cyanoimino)[(1,2,2-trimethylpropyl)amino]methyl]amino]-N-(phenylmethyl)benzamide.

20. A compound of claim 1 having the name 4-[[(cyanoimino)[(1,2,2-trimethylpropyl)amino]methyl]amino]-N,N-dimethylbenzamide.

21. A compound of claim 1 having the name N-cyano-N'-[4-(1-piperidinylcarbonyl)phenyl]-N''-(1,2,2-trimethylpropyl)guanidine.

22. A compound of claim 1 having the name N-cyano-N'-[4-(4-morpholinylcarbonyl)phenyl]-N''-(1,2,2-trimethylpropyl)guanidine.

23. A compound of claim 1 having the name N-cyano-N'-[4-(4-thiomorpholinylcarbonyl)phenyl]-N''-(1,2,2-trimethylpropyl)guanidine.

24. A compound of claim 1 having the name N-cyano-N'-[4-[4-(phenylmethyl)-1-piperazinyl]-carbonyl]phenyl]-N''-(1,2,2-trimethyl-propyl)guanidine.

25. A compound of claim 1 having the name N-cyano-N'-(5,6,7,8-tetrahydro-5-oxo-2-naphthalenyl)-N''-(1,2,2-trimethylpropyl)guanidine.

26. A compound of claim 1 having the name N-cyano-N'-(1,1-dimethylethyl)-N''-(1,2,3,4-tetrahydro -2-methyl-1-oxo-6-isoquinolinyl)guanidine.

27. A compound of claim 1 having the name N-cyano-N'-(1,1-dimethylpropyl)-N''-3-(methylsulfonyl)-phenyl]guanidine.

28. A compound of claim 1 having the name N-cyano-N'-(1,1-dimethylpropyl)-N''-3-(methylsulfinyl)-phenyl]guanidine.

29. A compound of claim 1 having the name N-(3-chloro-4-nitrophenyl)-N'-cyano-N''-(1,1-dimethylethyl)guanidine.

30. A compound of claim 1 having the name N-cyano-N'-(4-fluoro-3-nitrophenyl)-N''-(1,1-dimethylethyl)guanidine.

31. A compound of claim 1 having the name N-cyano-N'-(4-cyano-3-methoxyphenyl)-N''-(1,2,2-trimethylpropyl)guanidine.

32. A compound of claim 1 having the name N-(3-chloro-4-cyanophenyl)-N'-cyano-N''-(1,1-dimethylethyl)guanidine.

33. A compound of claim 1 having the name N-cyano-N'-(l-cyclohexylethyl)-N''-[2-(trifluoromethyl)phenyl]guanidine.

34. A compound of claim 1 having the name N-cyano-N'-(4-cyanophenyl)-N''-(2-cyclohexyl-1-methylethyl)guanidine.

35. A composition useful in reducing blood pressure in a mammal and having decreased cardiac effects, comprising a pharmaceutically acceptable carrier and an antihypertensively effective amount of a compound of the formula including tautomeric forms and pharmaceutically acceptable salts thereof, wherein $R, R_1, R_2,$ and $R_3$ and $R_4$ are as defined in claim 1.

36. A method of reducing blood pressure in a mammal comprising administering an effective amount of the composition of claim 35.

* * * * *

UNITED STATES PATENT AND TRADEMARK OFFICE
CERTIFICATE OF CORRECTION

PATENT NO. : 5,011,837
DATED : April 30, 1991
INVENTOR(S) : Atwal et al.

It is certified that error appears in the above-identified patent and that said Letters Patent is hereby corrected as shown below:

Column 17, line 42, after "-NHarylalkyl" the following should be inserted --m = 1 or 2, and $R_5$ is hydrogen or $R_1$--;

Column 18, lines 48-50, the name should read:
--N-cyano-N'-[4-[[4-(phenylmethyl)-1-piperazinyl]-carbonyl]-phenyl]-N"-(1,2,2-trimethyl-propyl)guanidine--;

Column 18, lines 57-59; the name should read:
--N-cyano-N'-(1,1-dimethylpropyl)-N"-[3-(methylsulfonyl)-phenyl]guanidine--;

Column 18, lines 60-62; the name should read:
--N-cyano-N'-(1,1-dimethylpropyl)-N"-[3-(methylsulfinyl)-phenyl]guanidine--.

Signed and Sealed this

Thirteenth Day of July, 1993

Attest:

MICHAEL K. KIRK

*Attesting Officer*   Acting Commissioner of Patents and Trademarks